US008666766B2

(12) United States Patent  (10) Patent No.: US 8,666,766 B2
Guillama et al.  (45) Date of Patent: Mar. 4, 2014

(54) SYSTEM AND METHODS FOR SIMULATING FUTURE MEDICAL EPISODES

(75) Inventors: Noel Guillama, Wellington, FL (US); Chester Heath, Boca Raton, FL (US); Pedro Martinez, Boca Raton, FL (US)

(73) Assignees: The Quantum Group, Inc., Wellington, FL (US); Noel J. Guillama, Wellington, FL (US)

( * ) Notice: Subject to any disclaimer, the term of this patent is extended or adjusted under 35 U.S.C. 154(b) by 494 days.

(21) Appl. No.: 12/535,523

(22) Filed: Aug. 4, 2009

(65) Prior Publication Data

US 2010/0161347 A1  Jun. 24, 2010

Related U.S. Application Data

(60) Provisional application No. 61/086,609, filed on Aug. 6, 2008.

(51) Int. Cl.
*G06Q 10/00* (2012.01)

(52) U.S. Cl.
USPC .................................. 705/2; 705/3

(58) Field of Classification Search
USPC ............................................. 705/2
See application file for complete search history.

(56) References Cited

U.S. PATENT DOCUMENTS 5,937,387 A * 8/1999 Summerell et al. ............ 705/2

* cited by examiner

Primary Examiner — Hiep V Nguyen
(74) Attorney, Agent, or Firm — Novak Druce Connolly Bove + Quigg LLP

(57) ABSTRACT

A computer-implemented method of generating future medical episodic simulations is provided. The method includes generating a personal wellness lifestyle signature for an individual based upon pre-selected data pertinent to wellness of the individual. Additionally, the method includes comparing the personal wellness lifestyle signature of the individual with at least one personal wellness lifestyle signature of at least one other individual determined to have at least one wellness characteristic similar to a corresponding wellness characteristic of the individual. The method further includes predicting at least one future medical episode corresponding to the individual based upon the comparison.

A computer-based system for generating future medical episodic simulations is also provided. The system includes one or more one processors having logic circuitry for processing data. The system also includes a signature-generating module configured to execute on the at least one processor for generating a personal wellness lifestyle signature for an individual based upon pre-selected data pertinent to wellness of the individual. Additionally, the system includes a comparing module configured to execute on the at least one processor for comparing the personal wellness lifestyle signature of the individual with at least one personal wellness lifestyle signature of at least one other individual determined to have at least one wellness characteristic similar to a corresponding wellness characteristic of the individual. The system further includes an episode-predicting module configured to execute on the at least one processor for predicting at least one future medical episode corresponding to the individual based upon the comparison.

28 Claims, 9 Drawing Sheets

400

SYSTEM AND METHODS FOR SIMULATING FUTURE MEDICAL EPISODES

CROSS-REFERENCE TO RELATED APPLICATIONS

This application claims the benefit of U.S. Provisional Patent Application No. 61/086,609, which was filed Aug. 6, 2008, and which is incorporated herein in its entirety.

FIELD OF THE INVENTION

The present invention is related to the field of data processing, and more particularly, to systems and method of predicting the future wellness of an individual or a patient.

BACKGROUND OF THE INVENTION

A significant challenge facing healthcare professionals endeavoring to maintain a patient's health is to convince the patient of potential medical outcomes stemming from the patient's behavior and lifestyle. Indeed, not a few health experts have ranked lifestyle as an even greater determinant of health and wellness, long term at least, than genetics, heredity, and family histories combined. To be convinced, though, the patient must accurately perceive the potential outcomes, the probabilities of the potential outcomes, and the factors that make each more or less likely.

With respect to even a single patient, providing a statistically-defensible predictions of possible health outcomes typically requires the collating and assessment of health-related medical and lifestyle information. Such information, even individual-specific information, can be generated over long periods and, usually, is extraordinarily voluminous. Typically, the information is only obtainable from disparate sources.

Today there is not an effective and efficient technique for providing lifestyle alternatives simulations. It is thus often difficult to provide to the patient a compelling picture that lays out the need to alter one or more lifestyle factors. Many, if not most, patients typically exist in at least a partial state of denial over the importance of such factors. This tends to be especially true with younger patients noted for misconstruing youth as absolute invulnerability. The absence of techniques for making complex mathematical and statistical evaluations of such information also precludes opportunities to discover unknown maladies, whether created by nature or caused by man-made factors. That is there are no effective and efficient mechanisms for generating predictive analyses based on lifestyle and medical histories possibly prevents the uncovering of hidden maladies. Moreover, there do not yet exist effective and efficient mechanisms for generating models of wellness based on such factors, let alone any mechanism for fine tuning such models based upon iteratively-applied feedback.

SUMMARY OF THE INVENTION

In view of the foregoing background, it is therefore a feature of the invention to provide systems and methods for providing medical episodic simulations. One aspect of the invention is the computer-based implementation of techniques for simulating and/or predicting future medical episodes pertaining to an individual or patient. As described herein, such simulations and predictions can be based on complex mathematical and/or statistical comparisons of wellness data specific to the individual or patient with data pertaining to numerous other similarly-situated individuals. Thus, statistically-defendable and valid predictions can be generated. Accordingly, the future health and wellness of the individual or patient can be estimated with a degree of confidence.

Another aspect of the invention is the generation, through simulation, of a compelling picture of what the individual's or patient's future health is likely to be given the individual's or patient's current wellness and lifestyle. Another aspect is the generation of a model of the individual's or patient's wellness. The model can be fine tuned using one or more feedback loops to elucidate outcomes likely to follow by the individual or patient following or not following the advice of a professional healthcare giver. Still another aspect of the invention is the integration of disparate medical and non-medical data from a wide array of data sources so as to readily identify disease patterns.

One embodiment of the invention is a computer-based system for generating future medical episodic simulations. The system can include at least one processor comprising logic-based circuitry for processing data according to a set of stored instructions. The system also can include a signature-generating module configured to execute on the at least one processor for generating a personal wellness lifestyle signature for an individual based upon pre-selected data pertinent to wellness of the individual. Additionally, the system can include a comparing module configured to execute on the at least one processor for comparing the personal wellness lifestyle signature of the individual with at least one personal wellness lifestyle signature of at least one other individual determined to have at least one wellness characteristic similar to a corresponding wellness characteristic of the individual. The system can further include an episode-predicting module configured to execute on the at least one processor for predicting at least one future medical episode corresponding to the individual based upon the comparison.

Another embodiment of the invention is a computer-implemented method of generating future medical episodic simulations. The method can include generating a personal wellness lifestyle signature for an individual based upon pre-selected data pertinent to wellness of the individual. The method also can include comparing the personal wellness lifestyle signature of the individual with at least one personal wellness lifestyle signature of at least one other individual determined to have at least one wellness characteristic similar to a corresponding wellness characteristic of the individual. The method can further include predicting at least one future medical episode corresponding to the individual based upon the comparison.

Yet another embodiment of the invention is a computer-readable medium in which is embedded computer-readable code, defining a computer program, that when loaded on a computer causes the computer to perform the following steps: generating a personal wellness lifestyle signature for an individual based upon pre-selected data pertinent to wellness of the individual; comparing the personal wellness lifestyle signature of the individual with at least one personal wellness lifestyle signature of at least one other individual determined to have at least one wellness characteristic similar to a corresponding wellness characteristic of the individual; and predicting at least one future medical episode corresponding to the individual based upon the comparison.

BRIEF DESCRIPTION OF THE DRAWINGS

There are shown in the drawings, embodiments which are presently preferred. It is expressly noted, however, that the invention is not limited to the precise arrangements and instrumentalities shown in the drawings.

DETAILED DESCRIPTION

The present invention is directed to systems and methods providing medical episodic simulations. Such systems and methods can implement, for example, techniques by which lifestyle alternatives can be simulated for predicting future medical episodes pertaining to an individual or patient. These simulations and predictions, moreover, can be based on complex mathematical and/or statistical comparisons of individual-specific wellness data of the individual or patient with those of numerous other similarly-situated individuals so as to generate statistically-defendable and valid predictions. Accordingly, in various embodiments of the invention, future health and wellness of the individual or patient can be estimated with a degree of confidence.

The system and methods also can be used to generate for the individual, through the simulation, a compelling picture of what the individual's or patient's future health can be expected to be given the individual's or patient's current wellness and lifestyle. The system and methods can, additionally or alternately, generate a model of the individual's or patient's wellness. Moreover, the model can be fine tuned using one or more feedback loops to elucidate outcomes likely to follow by the individual or patient following or not following professional medical advice. The system and methods, additionally or alternately, can be used to integrate disparate medical and non-medical data from a wide array of data sources to identify disease patterns.

System Aspects

Figure 1:
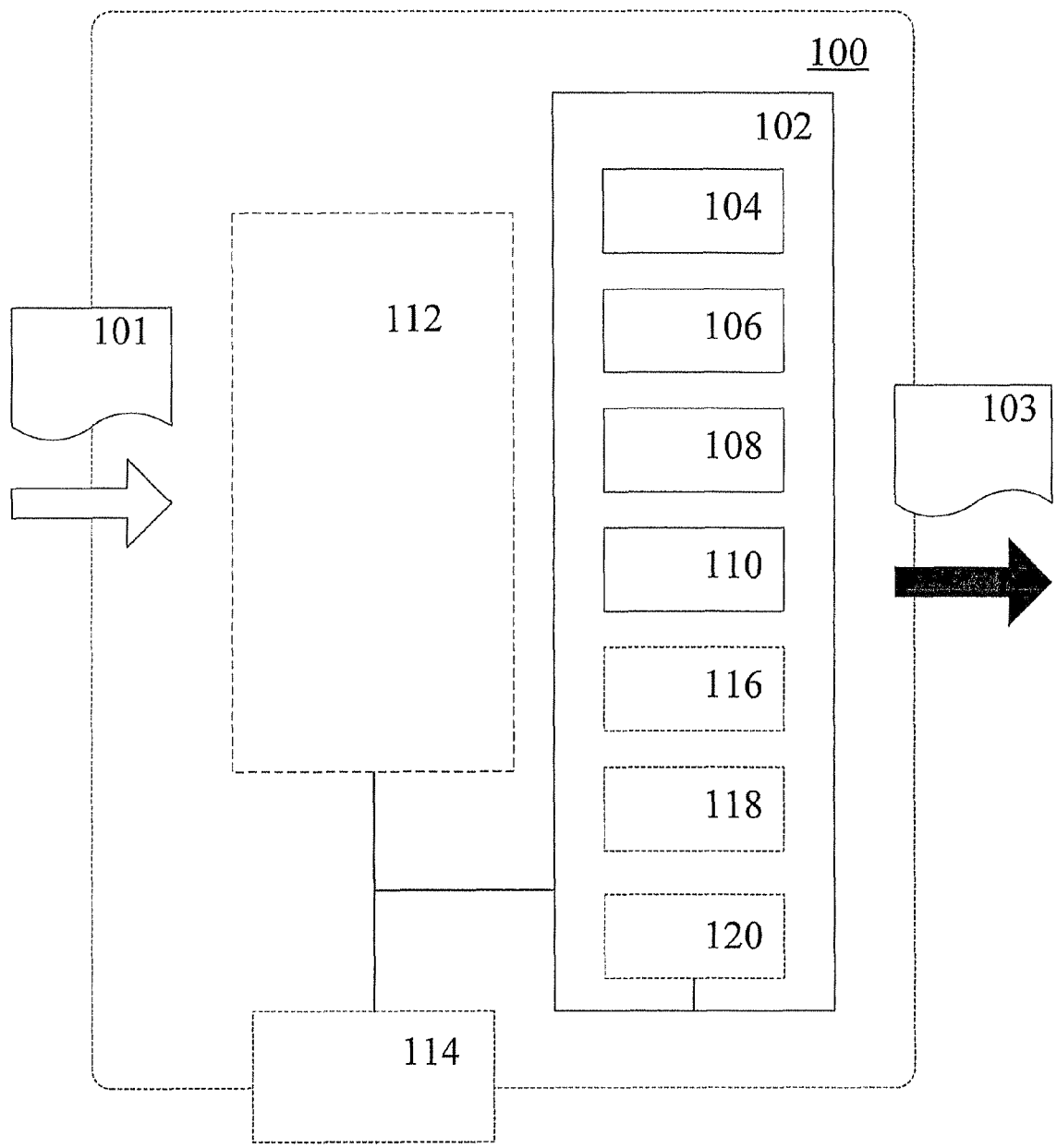
FIG. 1 is a schematic view of a system for generating future medical episodic simulations, according to one embodiment of the invention.

FIG. 1 is a schematic diagram of a computer-based system 100 for generating future medical episodic simulations, according to one embodiment of the invention. The system 100 illustratively includes one or more processors 102. As will be readily apparent to one of ordinary skill, the one or more processors 102 can be implemented in a single computing device or distributed among several devices that in the aggregate define a distributed system. The one or more processors can comprise registers, logic gates, controllers and other logic-based processing circuitry (not explicitly shown).

Illustratively, the system 100 further includes a signature-generating module 104, a signature-generating module 106, a comparing module 108, and an episode-predicting module 110 each configured to execute on the one or more processors 102 for performing the procedures, processes, and functions described herein. One or more of the signature-generating module 104, a signature-generating module 106, a comparing module 108, and an episode-predicting module 110 can be implemented as a combination of logic-based processing circuitry and processor-executable code, such as computer code configured to execute on a general purpose or application-specific computing device. In an alternative embodiment, however, one or more of the signature-generating module 104, a signature-generating module 106, a comparing module 108, and an episode-predicting module 110 can be implemented in hardwired dedicated circuitry configured to function cooperatively with a computing device for performing the same or similar procedures, processes, and functions As illustrated, the system 100 optionally includes one or more memory elements 112 communicatively linked to the one or more processors 102 for storing processor-executable instructions and/or data for processing according to the instructions. Illustratively, the system 100 further includes one or more input/output (I/O) devices 114, such as a keyboard, computer monitor, and/or computer mouse to enable a user to enter data, receive output.

Although illustratively shown as co-located with the one or more processors 102 within the system 100, in alternate embodiments, the one or more memory elements 112 like the one or more processors can be distributed at one or more remote sites forming a distributed environment. Accordingly, the one or more I/O devices 114 can comprise a network interface for communicatively link various remote sites through a network or interconnection of networks, such as the Internet.

Figure 2:
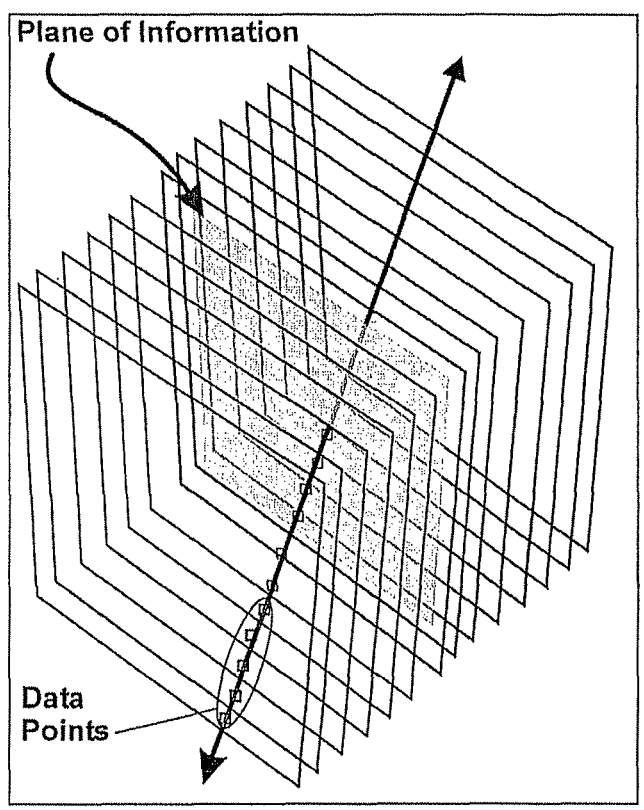
FIG. 2 is a schematic view of an exemplary data structure utilized by the system illustrated in FIG. 1.

A particular aspect of the system 100 is the generation and utilization of a personal wellness lifestyle signature (PWLS), which is described more particularly below. Over an individual's lifetime, an enormous quantity of medical and lifestyle information is generated pertaining to the individual. As described more particularly below, the system 100 can integrate and organize hyper-complex information generated over extended periods of time into a coherent data structure. Referring additionally to FIG. 2, an exemplary data structure is shown. The data structure 200 comprises a plurality of N-dimensional arrays (identified by the planes of information comprising multiple data points). Each such array can be parsed according to different pre-determined perspectives so as to generate reports pertinent to various disciplines. Additionally or alternatively, each such array can be mined to discover trends and associations, or reduced to any required level of understanding.

Figure 3:
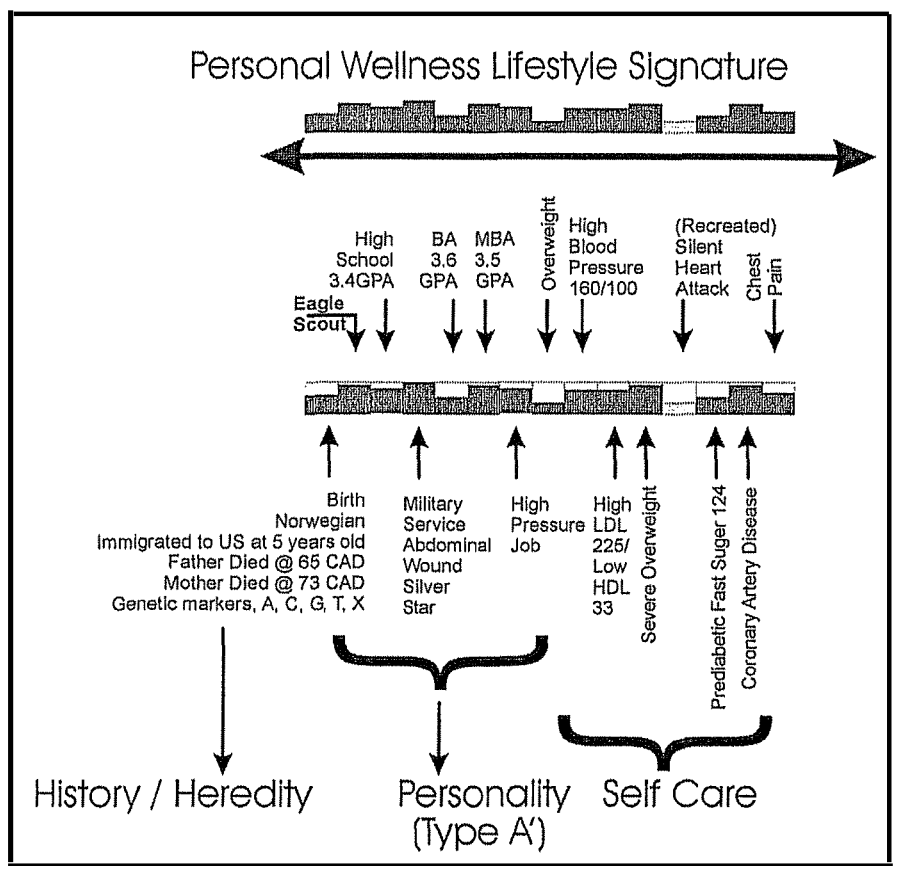
FIG. 3 is a schematic view of an exemplary personal wellness lifestyle signature (PWLS) generated and utilized by the system illustrated in FIG. 1.

One such report so generated by the system 100 is a PWLS for an individual or patient. Referring additionally to FIG. 3, an exemplary PWLS for a individual is shown. The PWLS can comprise and be integrated with various types of information so as to gain insight into the corresponding individual's health, lifestyle, and any other wellness-relevant information. Thus, the PWLS is an ideal vehicle for integrating various factors such as heredity, family history and the like. The PWLS can include various other factors as well, such as genetic markers and developmental attributes (e.g., birth weight and APGAR scores). Additionally, as described more particularly below in the context of the operative aspects of the system 100, data not conventionally considered medical can be mined to infer information where no specific data is available or testing has been performed. Though, illustrated as bar-chart values, it is to be noted that, in fact, each point of the PWLS comprises a vector having multiple dimensions that can compared to other vectors accurately and expeditiously using the computer-based system 100.

Referring specifically to FIG. 1, again, certain operative features of the invention are now described. Operatively, the signature-generating module 104 is configured to generate a personal wellness lifestyle signature for an individual based upon received, pre-selected data 101 pertinent to wellness of the individual. The comparing module 106 compares the personal wellness lifestyle signature of the individual with at least one personal wellness lifestyle signature of at least one other individual determined to have at least one wellness characteristic similar to a corresponding wellness characteristic of the individual. The episode-predicting module 108 generates a prediction 103, predicting at least one future medical episode corresponding to the individual based upon the comparison performed by the comparing module 106.

Optionally, the system 100 also can include an identifying module 116 configured to execute on the at least one processor 102. The identifying module 116 can be configured to identify the at least one other individual. More particularly, the identifying module 116 can be configured to identify the at least one other individual by determining a statistical correlation between the at least one wellness characteristic of the at least one other individual and the corresponding wellness characteristic of the individual. In a particular embodiment, the identifying module 116 can be configured to compute the statistical correlation by computing a value of a correlation coefficient and comparing the computed correlation coefficient to a predetermined level of similarity.

The system 100 can optionally, either additionally or alternatively, include a data mining module 118 configured to execute on the one or more processors 102. The data mining module 118, more particularly, can perform one or more data mining procedures so as to identify data indicative of the wellness of the individual. The data mining module 118 can be configured to perform data mining on one or more data sets. The data sets can include, for example, environmental data, lifestyle data, medical history data, and/or medical data.

Figure 4:
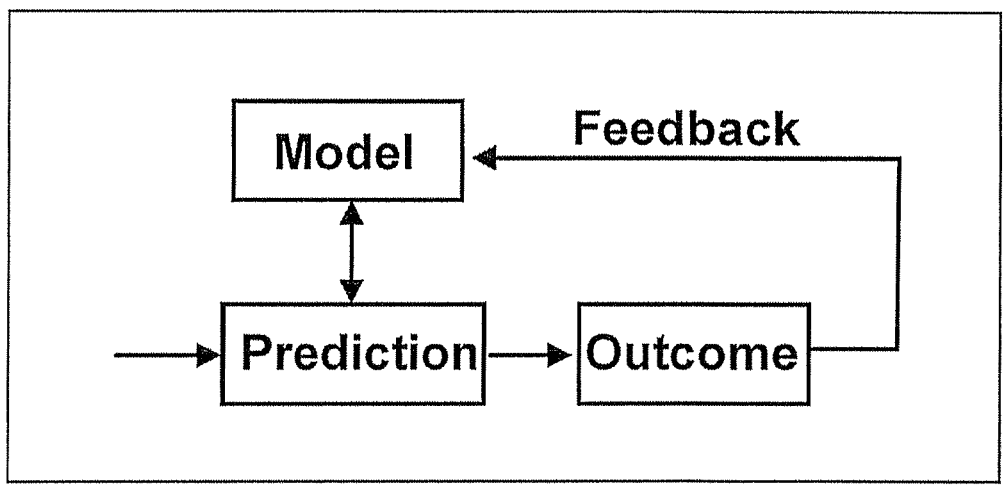
FIG. 4 is a schematic view of a wellness modeler, including feedback loop, according to another embodiment of the invention.

Optionally, the system 100 can additionally or alternately, include a wellness modeler 120 configured to execute on the one or more processors 102. The wellness modeler 120 can be configured to generate a model of the wellness of the individual. The model so generated by the wellness modeler 120 can be based upon at least one among a lifestyle history of the individual, a medical history of the individual, and past medical episodes of the individual. According to a particular embodiment comprising the wellness modeler 120, the system 100 can further include a feedback loop configured to refine the wellness model, as schematically illustrated in FIG. 4.

According to a particular embodiment, the wellness modeler 120 is configured to generate a statistical model. The wellness modeler 120, moreover, can be is configured to generate the statistical model by determining at least one factor weights.

EXAMPLES

Example 1

Operative aspects of the invention can be illustrated by example. Assumed in this example is an individual, Jon Docowitz, who was born to a family with a history of coronary artery disease and whose parents lived less than a normal lifespan. Jon was a high achiever from an early age, overcoming a language impairment (starting school speaking only a foreign language) to attain high grades, Eagle Scout, and a graduate degree with honors. He was also a decorated war hero, whose military record shows extraordinary drive. Jon was headed for success, but most likely a Type A personality headed for heart disease as well.

Jon's occupation placed continuous emotional stress on his body. The body reacted with high blood pressure. He gained weight; his blood chemistry showed the effects of stress and poor diet as he gained even more. Later results imply a silent heart attack sometime between two physical exams. Eventually his sugar tolerance indicated he was pre-diabetic; he was diagnosed with coronary artery disease and suffered chest pain. His physician, seeing the inevitable, advised him to lose weight, exercise, change his diet, and change his occupation. In denial, Jon sees a promotion near and says he does not have time to take care of himself. He asks for some pills to make his symptoms go away.

Figure 5:
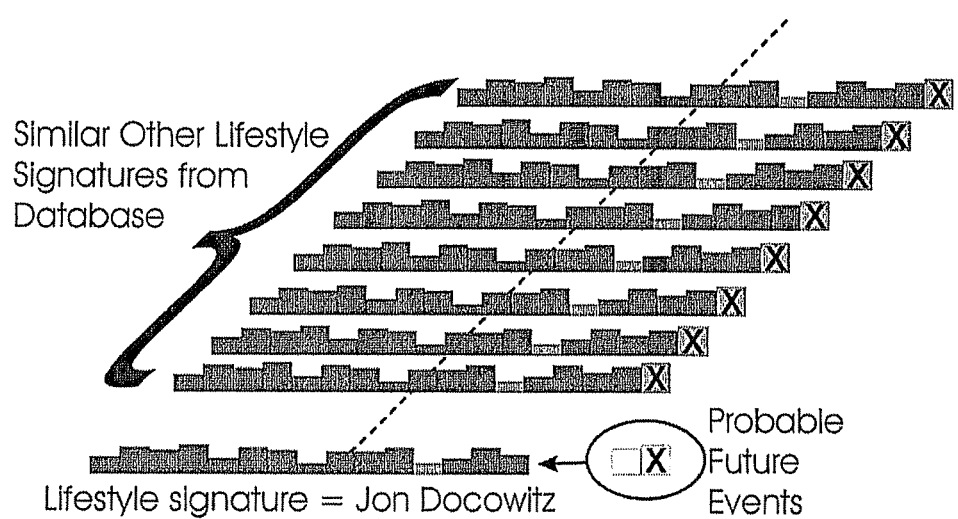
FIG. 5 is a schematic view of a representative PWLS.

Normally, the physician would not have tools to break down the denial. However, in this case, he does. "Mr. Docowitz, I took the liberty of ordering a report from a service that compares your lifestyle to others like you. Of nearly 130 million people, while none can match your military record, 7,225 individuals had lifestyles that correlated within 99.3% to yours—up to this point. They are all now dead!" The future medical episodic simulation relied on by the physician was generated by the system 100 described. The system 100 generated the exemplary PWLS 500 shown in FIG. 5

Continuing, the physician informed Jon that "based on their histories, the report suggests within a certainty of 70% that you will have a major heart attack sometime between 14 and 16 months from now. A second one will kill you shortly afterward. However, if you follow our advice your lifestyle will fall into another group of patients who listened to their doctors and lived an average of an additional 22 years. Now do you want that promotion enough to die for it?"

Example 2

Another example assumes a representative individual, Bette Dia, who began singing at age 4. By 16, blue eyed and frail, she was a graduate of Juilliard, a student at NYU and already quite a popular vocalist in jazz clubs about the City. Only casual exploitation of her talent made her a celebrity, well paid and indeed entitled to the best in food and drink wherever she performed, with little criticism as to her lifestyle and escapades. Her eventual rotund figure only enhanced her image as an artist. Yet, when, her nightlife was limited by increasing tiredness, her thirst increased and her vision blurred, her doctor was the first ever to criticize her lifestyle. She was not yet diabetic, but on her way. She had to give up some of the fruits of the good life or have much less life to live overall. It was not easy for a person used to living her way.

Figure 6:
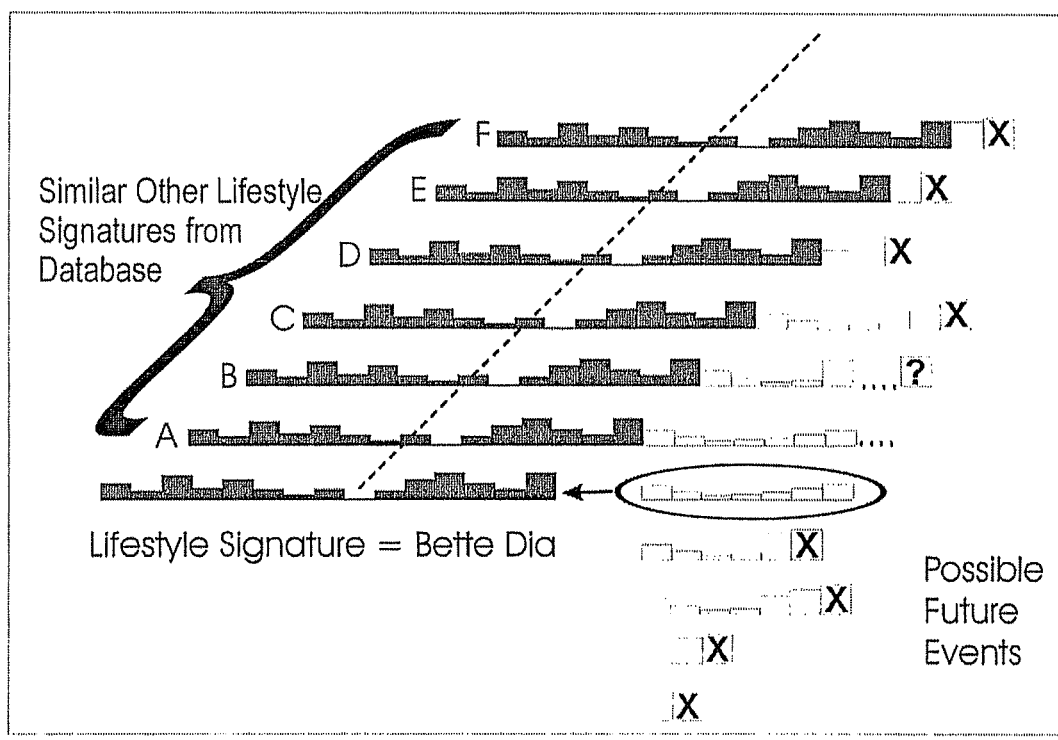
FIG. 6 is a schematic view of a representative PWLS.

Using an embodiment of the above-described system 100, Bette's doctor was able to show statistical alternatives; the disease was potentially avoidable and perhaps reversible to a normal life expectancy as with group A. The disease could be controlled, but potentially even a simple wound or other unanticipated complication could still lead to a wellness decline as with group B. Typically, a commitment to lifestyle change should lead to a significant extension of lifespan as in group C. Yet, without 2 hours of exercise per week, less than 30 percent of calories from fat and a loss of 7% weight within a year, she would fall into groups D through F. Almost certainly she would lose her 4-octave voice. Operatively, the system 100 can generate for Bette and her physician the exemplary PWLS 600 illustrated in FIG. 6. In response to the compelling picture provided, Bette is today known as the skinny soprano.

Example 3

Figure 7:
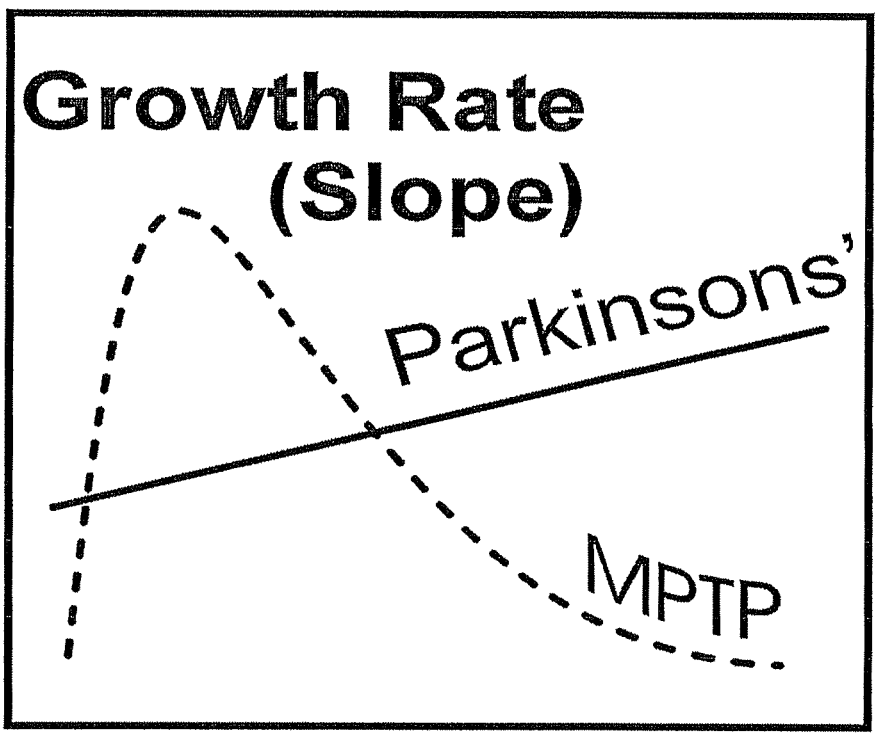
FIG. 7 is a plot contrasting selected characteristic of users of N-methyl-4-phenyl-1,2,3,6 tetrahydropyridine (MPTP).

Yet another example corresponds to actual events. Having been developed in a home laboratory, unknown and as yet unclassified by the DEA, a potent variation of the pain killer Demerol was legally available as a street drug. A contaminant in the homebrew narcotic called N-methyl-4-phenyl-1,2,3,6-tetrahydropyridine or (MPTP) was leading to near instantaneous destruction of a part of the brain that gates muscular control of the body. The symptoms of apparent total paralysis were nearly identical to advanced Parkinson's disease, yet the victims were in their teens and 20s rather than late in life. Indeed, there was no correlation between young and old lifestyle signatures, except all the young victims were street drug users. They also responded to L-Dopa treatment, as if they had advanced Parkinson's paralysis. And the growth slope of MPTP incidents was high initially and tapered off later perhaps as word spread among the street community of the bad drugs. (See FIG. 7.) The experience was repeated in northern California, Maryland and British Columbia all with the same characteristic growth curve. Several people would eventually die or be paralyzed for life.

Figure 8:
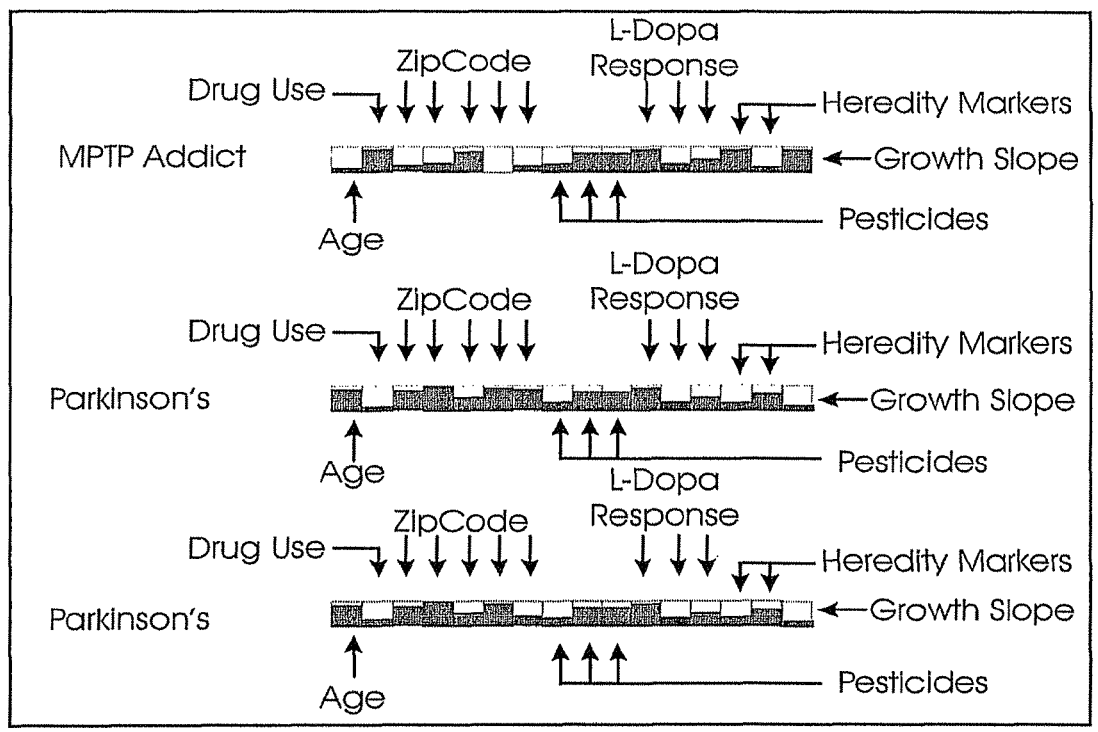
FIG. 8 is a PWLS incorporating characteristics corresponding to the plot of FIG. 7.

Statistical analysis of the lifestyle signatures of the older victims showed that true Parkinson's victims were 3 times more likely to acquire Parkinson's paralysis, if they lived much of their life at a zip code near a paper mill, 3 times more likely if they lived in rural agricultural zip codes—rather than a city, and 9 times more probable if they lived in both areas. Further statistical analysis showed that there were no recorded incidents of Parkinson's prior to 1910. The system 100 described above provides an all-inclusive, effective and efficient mechanism for obtaining the analysis. An exemplary PLWS 800 corresponding to the described scenario is shown in FIG. 8.

True Parkinson's was apparently an environmental disease, where MPTP was a mass poisoning. The street drug dealer was identified by victims who regained the ability to speak and move with Parkinson's treatments and removed from society when signatures of victims in a new zip code showed the high slope characteristic of the initial phase of distribution.

As already described the processes, procedures and functions implemented by the above-described system 100, utilize PWLSs, combined with other statistical evidence, so as to identify the trend and predict an outbreak rapidly and for much less cost. Further, the statistical associations to Parkinson's paralysis by geography and/or heredity and environmental factors came afterward, only because researchers knew to look for an environmental- or chemical-based causality factor. Otherwise the causes of Parkinson's might be much less understood now.

More generally, the system 100 provides a mechanism for predictive analysis of the medical history to identify and predict trends pertaining to maladies, whether created in nature or in response to man-made conditions. As already noted, an optional aspect of the system is a mechanism to utilize feedback on the data so as to optimize health-related models. Rather than simple comparison, factors can be heuristically weighted with experience to increase the validity of the simulations and estimations generated by the system 100.

Method Aspects

Figure 9:
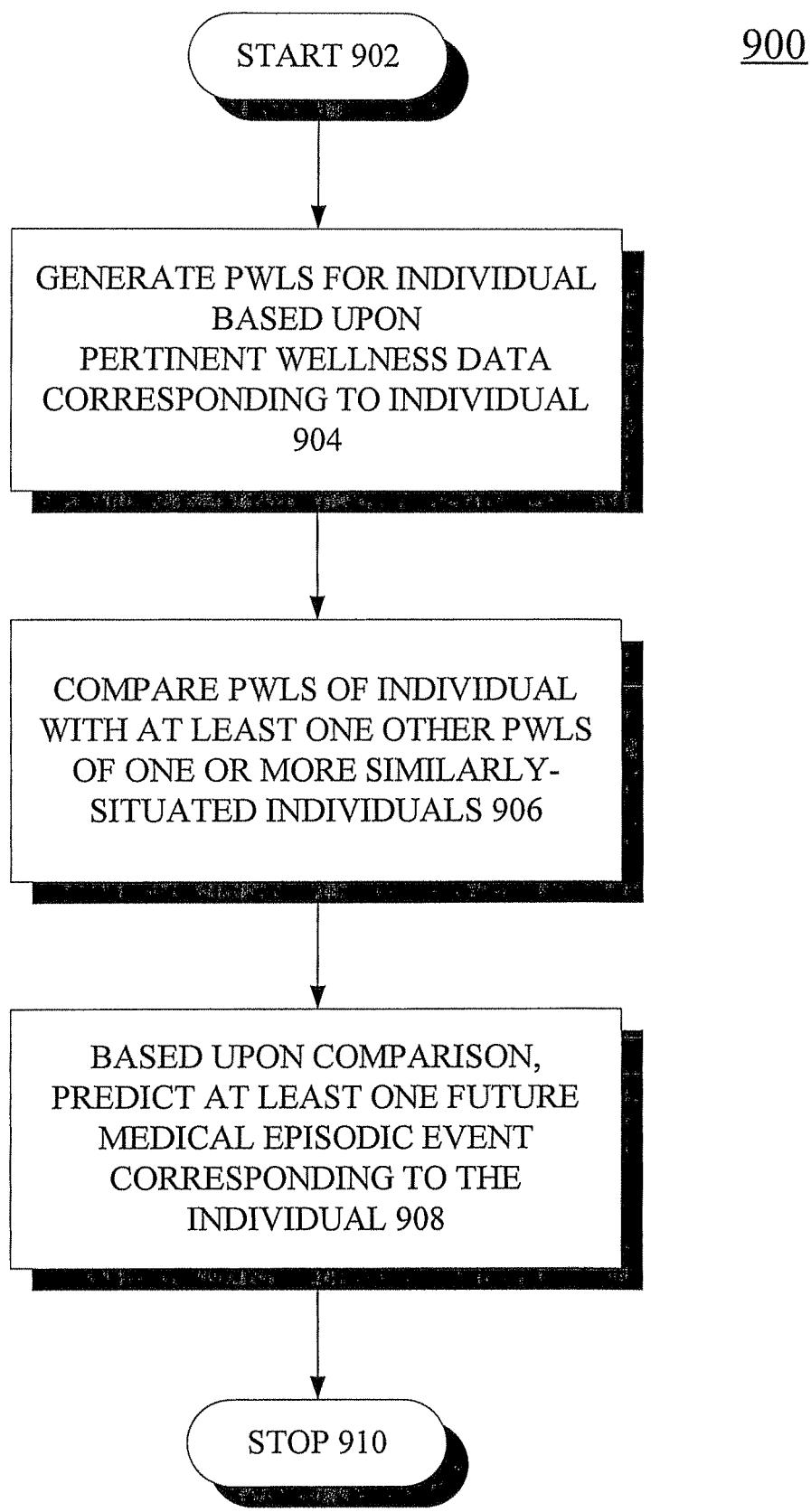
FIG. 9 is a flowchart of exemplary steps in a method for generating future medical episodic simulations, according to still another embodiment of the invention.

Referring now to FIG. 9, certain method aspects of the invention are illustrated. FIG. 9 is a flowchart of exemplary steps in a computer-implemented method of generating future medical episodic simulations, according to yet another embodiment of the invention.

The method 900 illustratively includes, after the start at block 902, generating a personal wellness lifestyle signature for an individual at block 904. The personal wellness lifestyle signature is based upon pre-selected data pertinent to wellness of the individual, as already described.

The method 900 further illustratively includes comparing the personal wellness lifestyle signature of the individual with at least one personal wellness lifestyle signature of at least one other individual at block 906. The at least one other individual is one determined to have at least one wellness characteristic similar to a corresponding wellness characteristic of the individual. Additionally, the method 900 includes, at block 908, predicting at least one future medical episode corresponding to the individual based upon the comparison. The method illustratively concludes at block 910.

According to one embodiment, the method 900 further includes identifying the at least one other individual by determining a statistical correlation between the at least one wellness characteristic of the at least one other individual and the corresponding wellness characteristic of the individual. The step of determining the statistical correlation can comprise computing a value of a correlation coefficient and comparing the computed correlation coefficient to a predetermined level of similarity.

According to still another embodiment, the method 900 further comprises performing at least one data mining step to identify data indicative of the wellness of the individual. Performing the at least one data mining step can comprise performing data mining on one or more data sets comprising at least one among environmental data, lifestyle, medical history data, and medical data.

According to yet another embodiment, the method 900 additionally includes generating a wellness model that models the wellness of the individual. The model so generated according to this step can be based upon at least one among lifestyle history of the individual, medical history of the individual, and past medical episodes of the individual. According to still another embodiment, the method 900 further comprises providing a feedback loop to refine the wellness model. Generating the wellness model can comprise generating a statistical model, according to a particular embodiment. According to this particular embodiment, generating the statistical model can further include determining at least one factor weight.

The invention, as already noted, can be realized in hardware, software, or a combination of hardware and software. The invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The invention, as also already noted, can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The foregoing description of preferred embodiments of the invention have been presented for the purposes of illustration. The description is not intended to limit the invention to the precise forms disclosed. Indeed, modifications and variations will be readily apparent from the foregoing description. Accordingly, it is intended that the scope of the invention not be limited by the detailed description provided herein.

We claim:

1. A computer-implemented method of generating future medical episodic simulations, the method comprising:
    performing, via a processor, the steps of:
        generating a personal wellness lifestyle signature for an individual based upon pre-selected data pertinent to wellness of the individual, the personal wellness lifestyle signature comprising a plurality of vectors representing information associated with a plurality of wellness characteristics based on the pre-selected data;
        identifying a plurality of other personal wellness lifestyle signatures for a plurality of other individuals determined to have at least one vector similar to a corresponding one of the plurality of vectors in the personal wellness lifestyle signature of the individual;
        obtaining correlation values for the personal wellness lifestyle signature of the individual with respect to each of the plurality of other personal wellness lifestyle signatures of the plurality of other individuals; and
        predicting a likelihood of the individual suffering from at least one medical episode based upon a portion of the plurality of other personal wellness lifestyle signatures associated with correlation values meeting a correlation criteria and an incidence of the at least one medical episode in the portion of the plurality of other individuals.

2. The method of claim 1, wherein obtaining the correlation values comprises determining a statistical correlation by computing a value of a correlation coefficient and comparing the computed correlation coefficient to a predetermined level of similarity.

3. The method of claim 1, the steps further comprising performing at least one data mining step to identify data indicative of the wellness of the individual.

4. The method of claim 3, wherein performing the at least one data mining step comprises performing data mining on one or more data sets comprising at least one among environmental data, lifestyle, medical history data, and medical data.

5. The method of claim 1, the steps further comprising generating a wellness model that models the wellness of the individual, the model being based upon at least one among lifestyle history of the individual, medical history of the individual, and past medical episodes of the individual.

6. The method of claim 5, further comprising providing a feedback loop to refine the wellness model.

7. The method of claim 5, wherein generating the wellness model comprises generating a statistical model.

8. The method of claim 7, wherein generating the statistical model comprises determining at least one factor weight.

9. The method of claim 5, further comprising the steps of computing at least one projected wellness lifestyle signature for the individual using the model and based on at least one change in a lifestyle of the individual; and repeating the steps of identifying, obtaining, and predicting for the at least one projected wellness lifestyle signature.

10. A computer-based system for generating future medical episodic simulations, the system comprising:
    at least one processor comprising logic circuitry for processing data;
    a computer readable storage medium storing instructions for controlling the processor to perform steps comprising:
        generating a personal wellness lifestyle signature for an individual based upon pre-selected data pertinent to wellness of the individual, the personal wellness lifestyle signature comprising a plurality of vectors representing information associated with a plurality of wellness characteristics based on the pre-selected data;
        identifying a plurality of other personal wellness lifestyle signatures for a plurality of other individuals determined to have at least one vector similar to a corresponding one of the plurality of vectors in the personal wellness lifestyle signature of the individual;
        obtaining correlation values for the personal wellness lifestyle signature of the individual with respect to each of the plurality of other personal wellness lifestyle signatures of the plurality of other individuals; and
        predicting a likelihood of the individual suffering from at least one medical episode based upon a portion of the plurality of other personal wellness lifestyle signatures associated with correlation values meeting a correlation criteria and an incidence of the at least one medical episode in the portion of the plurality of other individuals.

11. The system of claim 10, wherein obtaining the correlation values comprises computing a statistical correlation by computing a value of a correlation coefficient and comparing the computed correlation coefficient to a predetermined level of similarity.

12. The system of claim 10, the instructions for controlling the processor further comprising the step of performing at least one data mining procedure to identify data indicative of the wellness of the individual.

13. The system of claim 12, wherein the data mining performed on one or more data sets comprising at least one among environmental data, lifestyle, medical history data, and medical data.

14. The non-transitory computer-readable medium of claim 13, further comprising the steps of computing at least one projected wellness lifestyle signature for the individual using the model and based on at least one change in a lifestyle of the individual; and repeating the steps of identifying, obtaining, and predicting for the at least one projected wellness lifestyle signature.

15. The system of claim 10, the instructions for controlling the processor further comprising the step of generating a model of the wellness of the individual, the model being based upon at least one among lifestyle history of the individual, medical history of the individual, and past medical episodes of the individual.

16. The system of claim 15, further comprising a feedback loop configured to refine the wellness model.

17. The system of claim 15, wherein the generating of the wellness model generating a statistical model.

18. The system of claim 17, wherein generating the statistical model comprises determining at least one factor weight.

19. The method of claim 15, further comprising the steps of computing at least one projected wellness lifestyle signature for the individual using the model and based on at least one change in a lifestyle of the individual; and repeating the steps of identifying, obtaining, and predicting for the at least one projected wellness lifestyle signature.

20. A non-transitory computer-readable medium in which is embedded computer-readable code, defining a computer program, that when loaded on a computer causes the computer to perform the steps of:

generating a personal wellness lifestyle signature for an individual based upon preselected data pertinent to wellness of the individual, the personal wellness lifestyle signature comprising a plurality of vectors representing information associated with a plurality of wellness characteristics based on the pre-selected data;

identifying a plurality of other personal wellness lifestyle signatures for a plurality of other individuals determined to have at least one vector similar to a corresponding one of the plurality of vectors in the personal wellness lifestyle signature of the individual;

obtaining correlation values for the personal wellness lifestyle signature of the individual with respect to each of the plurality of other personal wellness lifestyle signatures of the plurality of other individuals; and predicting a likelihood of the individual suffering from at least one medical episode based upon a portion of the plurality of other personal wellness lifestyle signatures associated with correlation values meeting a correlation criteria and an incidence of the at least one medical episode in the portion of the plurality of other individuals.

21. The non-transitory computer-readable medium of claim 20, wherein obtaining the correlation values comprises determining a statistical correlation by computing a value of a correlation coefficient and comparing the computed correlation coefficient to a predetermined level of similarity.

22. The non-transitory computer-readable medium of claim 20, further comprising performing at least one data mining step to identify data indicative of the wellness of the individual.

23. The non-transitory computer-readable medium of claim 22, wherein performing the at least one data mining step comprises performing data mining on one or more data sets comprising at least one among environmental data, lifestyle, medical history data, and medical data.

24. The non-transitory computer-readable medium of claim 20, further comprising generating a wellness model that models the wellness of the individual, the model being based upon at least one among lifestyle history of the individual, medical history of the individual, and past medical episodes of the individual.

25. The non-transitory computer-readable medium of claim 24, further comprising providing a feedback loop to refine the wellness model.

26. The non-transitory computer-readable medium of claim 24, wherein generating the wellness model comprises generating a statistical model.

27. The non-transitory computer-readable medium of claim 26, wherein generating the statistical model comprises determining at least one factor weight.

28. The non-transitory computer-readable medium of claim 26, wherein generating the statistical model disproportionately emphasizes at least one factor weight for the purpose of presentation.

* * * * *